United States Patent
Yang et al.

(10) Patent No.: US 11,879,124 B2
(45) Date of Patent: Jan. 23, 2024

(54) **CONSTRUCTION METHOD OF A TIGHT REGULATION SYSTEM FOR GENE EXPRESSION IN *ZYMOMONAS MOBILIS* AND APPLICATIONS**

(71) Applicant: Hubei University, Wuhan (CN)

(72) Inventors: Shihui Yang, Wuhan (CN); Yi Wang, Wuhan (CN); Yunhao Chen, Wuhan (CN); Yueyue Chen, Wuhan (CN); Qiaoning He, Wuhan (CN)

(73) Assignee: Hubei University, Wuhan (CN)

( * ) Notice: Subject to any disclaimer, the term of this patent is extended or adjusted under 35 U.S.C. 154(b) by 0 days.

(21) Appl. No.: 18/315,140

(22) Filed: May 10, 2023

(65) Prior Publication Data

US 2023/0287398 A1    Sep. 14, 2023

(30) Foreign Application Priority Data

Mar. 14, 2022    (CN) .......................... 202210248136.9

(51) Int. Cl.
| | | |
|---|---|---|
| *C12N 15/74* | (2006.01) | |
| *C12N 1/20* | (2006.01) | |
| *C12N 15/10* | (2006.01) | |
| *C12N 15/70* | (2006.01) | |

(52) U.S. Cl.
CPC ........... *C12N 15/1082* (2013.01); *C12N 1/20* (2013.01); *C12N 15/70* (2013.01); *C12N 15/74* (2013.01)

(58) Field of Classification Search
None
See application file for complete search history.

(56) References Cited

U.S. PATENT DOCUMENTS

2016/0168580 A1*  6/2016  Woo ....................... C12N 15/74
                                                               435/320.1
2019/0024099 A1    1/2019  Lu et al.

FOREIGN PATENT DOCUMENTS

| CN | 101565706 A | 10/2009 | | |
| CN | 102071228 A | 5/2011 | | |
| CN | 102286518 A | 12/2011 | | |
| CN | 104031932 A | 9/2014 | | |
| CN | 104109687 A | 10/2014 | | |
| CN | 104152482 A | 11/2014 | | |
| CN | 104212829 A | 12/2014 | | |
| CN | 108456688 A | 8/2018 | | |
| CN | 110358720 A | 10/2019 | | |
| EP | 2377928 A2 | * 10/2011 | ........... | C12N 9/1247 |
| WO | WO-2016005931 A1 | * 1/2016 | ............. | A01H 6/342 |
| WO | WO-2021177900 A1 | * 9/2021 | ............. | C12N 15/52 |

OTHER PUBLICATIONS

Yang S et al. Biotechnol Biofuels. May 2, 2018;11:125 (Year: 2018).*
Wycuff DR et al. Biochem. Jan. 1, 2000;277(1):67-73 (Year: 2000).*
Gauttam R et al. Microb Biotechnol. Nov. 2021;14(6):2659-2678 (Year: 2021).*
Kashani HH et al. Osong Public Health Res Perspect. Aug. 2015;6(4):256-60 (Year: 2015).*
Shilling PJ et al. Commun Biol. May 7, 2020;3(1):214 (Year: 2020).*
Title of the Item: "Synthetic Biology Journal" Publication date: Feb. 15, 2021 Name of the Author: Yang Yongfu et al. Article Title:"Progress and perspectives on developing Zymomonas mobilis as a chassis cell" Pages:pp. 59-90.

* cited by examiner

*Primary Examiner* — Neil P Hammell
*Assistant Examiner* — Douglas Charles Ryan
(74) *Attorney, Agent, or Firm* — Nitin Kaushik

(57) ABSTRACT

A construction method of a regulation system for gene expression in *Zymomonas mobilis* and applications are provided. The T7 expression system in *Zymomonas mobilis* has been constructed. The T7 expression system is used to construct a regulation circuit, help analyze the function of toxic genes and realize the regulation of metabolic pathways in *Zymomonas mobilis*. At the same time, shuttle plasmids that can be used in *Zymomonas mobilis* and *Escherichia coli*, also be constructed to facilitate the construction of plasmid and improve the expression efficiency of foreign genes in *Zymomonas mobilis*, laying a foundation for subsequent protein expression and secretion and metabolic engineering pathway optimization regulation.

2 Claims, 8 Drawing Sheets

Specification includes a Sequence Listing.

_US 11,879,124 B2_

CONSTRUCTION METHOD OF A TIGHT REGULATION SYSTEM FOR GENE EXPRESSION IN ZYMOMONAS MOBILIS AND APPLICATIONS

INCORPORATION BY REFERENCE STATEMENT REGARDING THE MATERIAL ELECTRONICALLY SUBMITTED

The contents of the electronic sequence listing (name of the XML file: sequencelisting.xml; size: 37,877 bytes and date of creation: Mar. 14, 2022) is herein incorporated by reference in its entirety.

CROSS-REFERENCE TO RELATED APPLICATIONS

This application claims priority to Chinese Patent Application NO: 202210248136.9, filed with China National Intellectual Property Administration on Mar. 14, 2022, the entire contents of which are incorporated herein by reference.

TECHNICAL FIELD

This disclosure relates to the biotechnology field. Specifically, this disclosure relates to a construction method of a regulation system for gene expression in *Zymomonas mobilis* and applications.

BACKGROUND

The statements herein provide background information relevant to the present disclosure only and do not necessarily constitute prior art.

Regulation of gene expression is a complicated process which includes multiple levels of regulation, such as the gene level, the transcriptional level, the posttranscriptional level, the translational level, and so on, as well as the temporal and spatial regulations of gene expression in cells. Nevertheless, due to the complexity of the regulation of the gene expression, it may be toxic or lethal to the host cells in the process of gene expression, which restricts the study of gene function or the establishment of cell models.

Despite of the development of different prokaryotic or eukaryotic cell expression regulatory systems, current system for the expression regulation still has some limitations. For example, for prokaryotes, their system for the expression regulation has a slow and inefficient induction process and is lack of induction specificity and precise regulation of expression, which limits the application of the expression system. Therefore, a tight gene regulation system is needed, so that the spatial and temporal expressions of genes can be strictly controlled efficiently and cell resources can be used effectively.

*Zymomonas mobilis*, a facultative anaerobic Gram-negative bacterium, is the only microorganisms known to undergo anaerobic fermentation through the Entner-Doudoroff (ED) pathway. *Zymomonas mobilis* has the characteristics with small genome, high ethanol yield, high tolerances of sugar and ethanol, broad scopes of growth temperature (24~45° C.) and pH (4.0~8.0). Given these characteristics, *Zymomonas mobilis* is widely used in the industrial production of bioethanol and other products.

In recent years, a large number of studies have been carried out in the aspects of system biology and synthetic biology, genetic engineering and metabolic engineering for *Zymomonas mobilis*. By the development of high-throughput sequencing technology, genome sequences of multiple strains of *Zymomonas mobilis* have been reported, updated and accurately annotated, and the rational transformation and development of microbial cell factories have also been guided by the construction of genome-level metabolic models. In addition, the development of heterologous CRISPR-Cas12a and the endogenous type I-F CRISPR-Cas genome editing systems offer new genetic tools for efficient strain construction.

At the same time, combining the dual-reporter system with omics data, a batch of strong, medium and weak constitutive promoters as well as ethanol-inducible promoters and RBS of different strengths have been successfully predicted and characterized. The development of *Zymomonas mobilis* as a cell factory is supported by these technologies and methods. However, the lack of a tight regulation system for the gene expression and metabolic pathway construction in *Zymomonas mobilis* limits the applications of *Zymomonas mobilis* in gene function analysis, circuit construction, and spatial and temporal regulations of metabolic pathways.

SUMMARY

Embodiments provide a construction method of a regulation system for the gene expression in *Zymomonas mobilis*. A recombinant plasmid is provided by a Gibson Reaction with pZM 39 (Genbank ID: CP023718) plasmid, T7 RNAP gene and araC gene. Among them, the inducible promoter $P_{BAD}$ is used as the promoter of the gene T7 RNAP, and the inducible promoter Ptet is used as the promoter of the gene araC. The recombinant plasmid is transformed into *Zymomonas mobilis* (*Zymomonas mobilis* subsp. *mobilis* ZM4, ZM4), and colonies are obtained to establish the T7 expression system in *Z. mobilis* ZM4.

In some embodiments, the gene fragment to be expressed is transferred into the established T7 expression system for expression in *Zymomonas mobilis* (ZM4).

In some embodiments, the gene fragment to be expressed is transferred into a shuttle plasmid for expression. The shuttle plasmid can shuttle in both *Zymomonas mobilis* (ZM4) and *Escherichia coli* (*E. coli*).

In some embodiments, the shuttle plasmid is obtained by replacing the f1 origin on *E. coli* pET22b or pET28a with a Zymo-replicon from *Zymomonas mobilis* (ZM4).

In some embodiments, the resistance gene of pET22b is replaced with the kanamycin resistance gene.

In some embodiments, the nucleotide sequence of the T7 RNAP gene is shown in SEQ ID NO.1, the nucleotide sequence of the $P_{BAD}$ is shown in SEQ ID NO.2, and the nucleotide sequence of the araC is shown in SEQ ID NO.3.

Embodiments also provide an application of a regulation system for the gene expression in *Zymomonas mobilis*, which is demonstrated by above-described embodiments.

Embodiments also provide an expression plasmid that can be transformed in both *Zymomonas mobilis* (ZM4) and *Escherichia coli* (*E. coli*). The expression plasmid is pTZ22b, obtained by replacing the f1 origin on *E. coli* pET22b with a Zymo-replicon from *Zymomonas mobilis* (ZM4), and replacing a resistance gene with a kanamycin resistance gene.

Embodiments also provide an expression plasmid that can shuttle in both *Zymomonas mobilis* (ZM4) and *Escherichia coli* (*E. coli*). The expression plasmid is pTZ28a, obtained by replacing the f1 origin on *E. coli* pET28a with a Zymo-replicon from *Zymomonas mobilis* (ZM4).

Embodiments also provide an application of *Zymomonas mobilis* for the gene expression by the expression plasmid as said above, that can be transformed in both *Zymomonas mobilis* (ZM4) and *Escherichia coli* (*E. coli*).

Embodiments have constructed a T7 expression system, that is applied to construct the tight regulated lines, analyze the function of toxic genes, and execute the tight regulations of metabolic pathways in *Zymomonas mobilis*.

Embodiments have constructed shuttle plasmids that can be transformed in both *Zymomonas mobilis* (ZM4) and *Escherichia coli* (*E. coli*). The shuttle plasmid can be used to facilitate the construction of plasmids and improve the expression efficiency of foreign genes, laying a solid foundation for the optimal regulation of protein expression and metabolic pathways in *Zymomonas mobilis* (ZM4).

The establishment of the T7 expression system will improve the gene regulation system and the genetic operation tool system of *Zymomonas mobilis*, and solve the lack of gene regulation system for *Zymomonas mobilis*, and provide more possibilities for gene function analysis, circuitry construction, and temporal and spatial regulation of metabolic pathway of *Zymomonas mobilis*.

Meanwhile, *Zymomonas mobilis* is a GRAS (generally regarded as safe) strain, it has the advantages as a safe protein expression system.

Meanwhile, as *Zymomonas mobilis* is a GRAS strain with relatively small genome and simple metabolites, it has advantages as a safe protein expression system and a cell factory for safe protein expression replacing the *Escherichia coli* (*E. coli*).

DETAILED DESCRIPTION OF THE EMBODIMENTS

Figure 1:
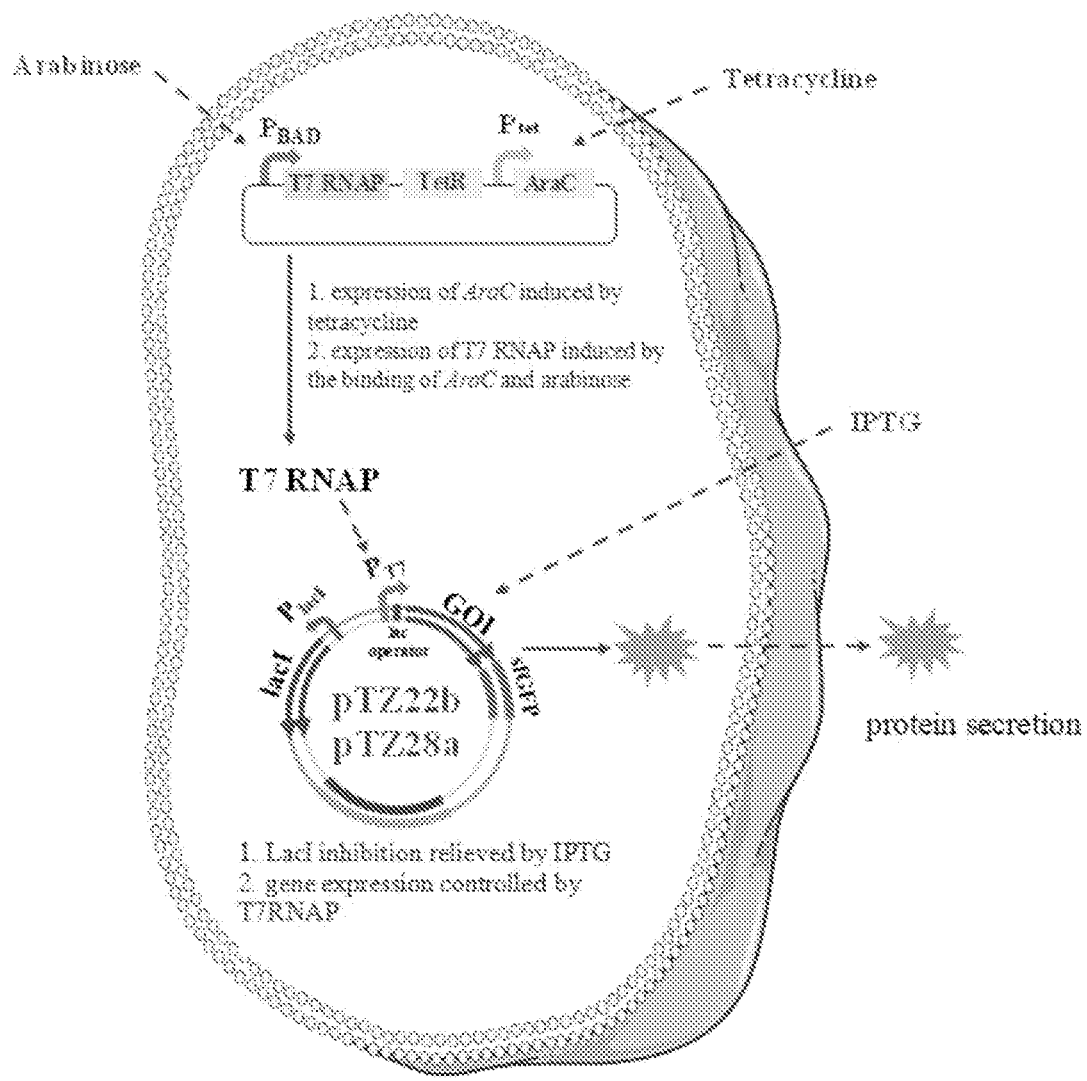
FIG. 1 illustrates a summary diagram of the project, in accordance with embodiments.

In order to make the objectives, technical scheme, and advantages of this disclosure clearer, this disclosure is further explained in details in combination with the following embodiments, and the following examples. The specific embodiments described herein are intended to explain this disclosure and are not intended to define this disclosure.

According to the information contained in this present disclosure, it is easy for those skilled in the art to make various changes to the precise description of this disclosure without departing from the spirit and scope of the attached claims. It should be understood that the scope of this disclosure is not limited to the defined process, nature, or component, as these embodiments and other descriptions are merely schematic descriptions of specific aspects of this disclosure. In fact, the various changes made by the person of ordinary skill in the art to the embodiment of this disclosure are covered within the scope of the attached claims.

In order to better understand this disclosure rather than limit the scope of this disclosure. Therefore, unless otherwise specified, the numerical parameters listed in the specification and the attached claims are approximate values, which may be changed depending on the desirable nature of the attempted acquisition. Each numerical parameter should be seen at least as obtained based on valid figures reported and by conventional rounding methods. In this disclosure, about refers to within 10% of a given value or range, preferably within 5%.

When the temperature is not specifically defined in the following embodiment of this present disclosure, it is all normal temperature conditions. Normal temperature refers to indoor temperature in the four seasons, without additional cooling or heating treatment, and the normal temperature is generally controlled at 10~30° C., preferably 15~25° C.

The genes, proteins, or fragments thereof involved in the present disclosure may be naturally purified products or chemically synthesized products, or generated from prokaryotic or eukaryotic hosts (e.g., bacteria, yeast, plants) using recombinant techniques.

Embodiments disclosed a construction method and application of a regulation system for the gene expression in *Zymomonas mobilis*. A shuttle plasmid expressing T7 RNA polymerase co-induced by both tetracycline and arabinose was constructed to accomplish the T7 expression system with strong orthogonality in *Zymomonas mobilis*. Simultaneously, shuttle plasmids (pTZ series plasmids) can be transformed into both *Zymomonas mobilis* (ZM4) and *Escherichia coli* (*E. coli*).

The shuttle plasmids were constructed by replacing the f1 origin on pET plasmids from *Escherichia coli* with a Zymoreplicon from *Zymomonas mobilis* (ZM4). The shuttle plasmids were capable of expressing foreign genes driven by $P_{T7}$.

In some embodiments, T7 expression was regulated due to its toxicity. T7 RNAP was controlled by promoter $P_{BAD}$, while araC expression was regulated by Ptet. In the absence of arabinose inducer, the target protein GFP was not expressed or its expression level was very low. The target protein expression level was high in the presence of both tetracycline and arabinose simultaneously.

In addition, the exogenous protein superfold green fluorescent protein (sfGFP) was selected to test its secretion ability in *Zymomonas mobilis*, which could achieve efficient expression and one-step secretion of the proteins to be expressed with the system established above.

The overall schematic diagram of the technical solution is shown in FIG. 1. The technical scheme of disclosure is described clearly and completely in combination with embodiments.

Step 1

In some embodiments, using pZM39 plasmid as vector, Gibson assembly was used to construct a recombinant plasmid for regulating the expression of T7 RNAP. The underlined part of the primer is the connecting homologous arm. The amplification system and procedures are shown in Table 1 and Table 2.

TABLE 1

PCR system

|  | 10 μL | 50 μL | Concentration |
| --- | --- | --- | --- |
| Primer F | 0.4 μL | 2 μL | 10 μM |
| Primer R | 0.4 μL | 2 μL | 10 μM |
| DNA | 0.2 μL | 1 μL | 20 ng~ |
| DNA polymerase | 5 μL | 25 μL | 1× |
| Milli-Q ultrapure water | Up to 10 μL | Up to 50 μL |  |

TABLE 2

PCR procedure

| Step | Temperature | Time | Cycle number |
| --- | --- | --- | --- |
| Pre-degeneration | 98° C. | 3 min | 1 |
| Denaturation | 98° C. | 10 s | 1 |
| Annealing | ~55° C. | 10 s | 1 |
| Extension | 72° C. | 5~10 s/kb | 25~32 |
| Terminal extension | 72° C. | 5 min | 1 |
| Temporary preservation | 4° C. | ∞ |  |

The T7 RNAP gene sequence used in this disclosure (after codon optimization) is as follows:

```
>T7 RNAP
                                           SEQ ID NO. 1
atgaacacgattaacatcgctaagaacgacttctctgacatcgaactggct
gctatcccgttcaacactctggctgaccattacggtgagcgtttagctcgc
gaacagttggcccttgagcatgagtcttacgagatgggtgaagcacgcttc
cgcaagatgtttgagcgtcaacttaaagctggtgaggttgcggataacgct
gccgccaagcctctcatcactaccctactccctaagatgattgcacgcatc
aacgactggtttgaggaagtgaaagctaagcgcggcaagcgcccgacagcc
ttccagttcctgcaagaaatcaagccggaagccgtagcgtacatcaccatt
aagaccactctggcttgcctaaccagtgctgacaatacaaccgttcaggct
gtagcaagcgcaatcggtcgggccattgaggacgaggctcgcttcggtcgt
atccgtgaccttgaagctaagcacttcaagaaaaacgttgaggaacaactc
aacaagcgcgtagggcacgtctacaagaaagcatttatgcaagttgtcgag
gctgacatgctctcaagggtctactcggtggcgaggcgtggtcttcgtgg
cataaggaagactctattcatgtaggagtacgctgcatcgagatgctcatt
gagtcaaccggaatggttagcttacaccgccaaatgctggcgtagtaggt
caagactctgagactatcgaactcgcacctgaatacgctgaggctatcgca
acccgtgcaggtgcgctggctggcatctctccgatgttccaaccttgcta
gttcctcctaagccgtggactggcattactggtggtggctattgggctaac
ggtcgtcgtcctctggcgctggtgcgtactcacagtaagaaagcactgatg
cgctacgaagacgtttacatgcctgaggtgtacaaagcgattaacattgcg
caaaacaccgcatgaaaatcaacaagaaagtcctagcggtcgccaacgta
atcaccaagtggaagcattgtccggtcgaggacatccctgcgattgagcgt
gaagaactcccgatgaaaccggaagacatcgacatgaatcctgaggctctc
accgcgtggaaacgtgctgccgctgctgtgtaccgcaaggacaaggctcgc
aagtctcgcgctatcagccttgagttcatgcttgagcaagccaataagttt
gctaaccataaggccatctggttcccttacaacatggactggcgcggtcgt
gtttacgctgtgtcaatgttcaacccgcaaggtaacgatatgaccaaagga
ctgcttacgctggcgaaaggtaaaccaatcggtaaggaaggttactactgg
ctgaaaatccacggtgcaaactgtgcgggtgtcgataaggttccgttccct
gagcgcatcaagttcattgaggaaaaccacgagaacatcatggcttgcgct
aagtctccactggagaacacttggtgggctgagcaagattctccgttctgc
ttccttgcgttctgctttgagtacgctggggtacagcaccacgcctgagc
tataactgctcccttccgctggcgtttgacgggtcttgctctggcatccag
cacttctccgcgatgctccgagatgaggtaggtggtcgcgcggttaacttg
cttcctagtgaaaccgttcaggacatctacgggattgttgctaagaaagtc
aacgagattctgcaggctgatgctatcaacgggaccgataacgaagtagtt
accgtgaccgatgagaacactggtgaaatctctgagaaagtcaagctgggc
actaaggcactggctggtcaatggctggcttacggtgttactcgcagtgtg
actaagcgttcagtcatgacgctggcttacgggtccaaagagttcggcttc
cgtcaacaagtgctggaagataccattcagccagctattgattccggcaag
ggtctgatgttcactcagccgaatcaggctgctggatacatggctaagctg
atttgggaatccgtttccgttaccgttgttgctgctgttgaagcaatgaac
tggcttaagtctgctgctaagctgctggctgctgaggtcaaagataagaag
actggagagattcttcgcaagcgttgcgctgtgcattgggtaactcctgat
ggtttccctgtgtggcaggaatacaagaagcctattcagacgcgcttgaac
ctgatgttcctcggtcagttccgcttacagcctaccattaacaccaacaaa
gatagcgagattgatgcacacaaacaggagtctggtatcgctcctaactt
gtacacagccaagacggtagccaccttcgtaagactgtagtgtgggcacac
gagaagtacggaatcgaatcttttgcactgattcacgactccttcggtacc
attccggctgacgctgcgaacctgttcaaagcagtgcgcgaaactatggtt
gacacatatgagtcttgtgatgtactggctgattctacgaccagttcgct
gaccagttgcacgagtcctcaattggacaaaatgccagcacttccggctaa
aggtaacttgaacctccgtgacatcttagagtcggacttcgcgttcgcgta
a,
```

Primers for amplifying fragment of T7 RNAP (including T7 terminator) were synthesized, named T7 RNAP-F and T7 RNAP-R.

T7 RNAP-F:
SEQ ID NO. 7
atgaacacgattaacatcgctaagaac,

T7 RNAP-R:
SEQ ID NO. 8
agtagtaggttgaggccgttga,

Inducible promoter P$_{BAD}$ was used as the promoter of gene T7 RNAP, shown as follows:

>P$_{BAD}$
SEQ ID NO. 2
aaaccaattgtccatattgcatcagacattgccgtcactgcgtctttta ctggctcttctcgctaaccaaaccggtaaccccgcttattaaaagcatt ctgtaacaaagcgggaccaaagccatgacaaaaacgcgtaacaaaagtg tctataatcacggcagaaaagtccacattgattatttgcacggcgtcac actttgctatgccatagcatttttatccataagattagcggatcctacc tgacgcttttatcgcaactctctactgtttctccataagtattcaaat gatctaaagaggagaaaggatctccc, Primers for amplifying the fragment of P$_{BAD}$ were synthesized, named P$_{BAD}$-F and P$_{BAD}$-R.

P$_{BAD}$-F:
SEQ ID NO. 9
cggccgcttctagag aaaccaattgtccatattgcatcagacattg,

P$_{BAD}$-R:
SEQ ID NO. 10
gatgttaatcgtgttcatgggagatcctttctcctctttag,

An inducible promoter Ptet was used as the promoter of gene araC, shown as follows:

>araC
SEQ ID NO. 3
atggctgaagcgcaaaatgatcccctgctgccgggatactcgtttaatgcc catctggtggcgggtttaacgccgattgaggccaacggttatctcgatttt tttatcgaccgaccgctgggaatgaaaggttatattctcaatctcaccatt cgcggtcaggggggtggtgaaaaatcagggacgagaatttgtttgccgaccg ggtgatattttgctgttcccgccaggagagattcatcactacggtcgtcat ccggaggctcgcgaatggtatcaccagtgggtttactttcgtccgcgcgcc tactggcatgaatggcttaactggccgtcaatatttgccaatacggggttc tttcgcccggatgaagcgcaccagccgcatttcagcgacctgtttgggcaa atcattaacgccgggcaaggggaagggcgctattcggagctgctggcgata aatctgcttgagcaattgttactgcggcgcatggaagcgattaacgagtcg ctccatccaccgatggataatcgggtacgcgaggcttgtcagtacatcagc gatcacctggcagacagcaattttgatatcgccagcgtcgcacagcatgtt tgcttgtcgccgtcgcgtctgtcacatctttccgccagcagttagggatt agcgtcttaagctggcgcgaggaccaacgtatcagccaggcgaagctgctt ttgagcaccacccggatgcctatcgccaccgtcggtcgcaatgttggtttt gacgatcaactctatttctcgcgggtatttaaaaaatgcaccggggccagc ccgagcgagttccgtgccggttgtgaagaaaaagtgaatgatgtagccgtc aagttgtcataa, TetR-F:
SEQ ID NO. 13
cctcaacctactactttaagacccactttcacatttaagttgttttttcta a, Ptet-R:
SEQ ID NO. 14
ttgcgcttcagccatgggagatccttctcctctttagatc, The recombinant plasmid vector was reversely amplified from pZM39, that the amplified reaction was implemented referred to Table 1 and Table 2. Primers for amplifying the fragment of pZM39 vector were synthesized, named 39p-F and 39p-R.

39p-F:
SEQ ID NO. 15
cgtcccatagatctcgagc,

39p-R:
SEQ ID NO. 16
ctctagaagcggccgcg,

The above fragments were ligated to the pZM39 vector by Gibson assembly. The sequence of fragment connection was P$_{BAD}$+T7 RNAP+TetR+Ptet+araC. The conjugated products were transformed into *Escherichia coli*. DH5a receptive cells were screened using plates containing antibiotics chloramphenicol (50 μg/mL). Colonies were selected the next day, and preliminarily verified by PCR using pEZ-dp-F (ctgaattcgcggccgc, SEQ ID NO.17) and pEZ-15A-R (cacttcactgacaccctcat, SEQ ID NO.18) as primers.

The recombinant plasmid was extracted from the colonies with expected band size (5012 bp) and overnight culture. The plasmid extraction process was referred to the standard steps of plasmid extraction kit. The recombinant plasmid obtained by preliminary verification and screening was further verified by sequencing.

Figure 2:
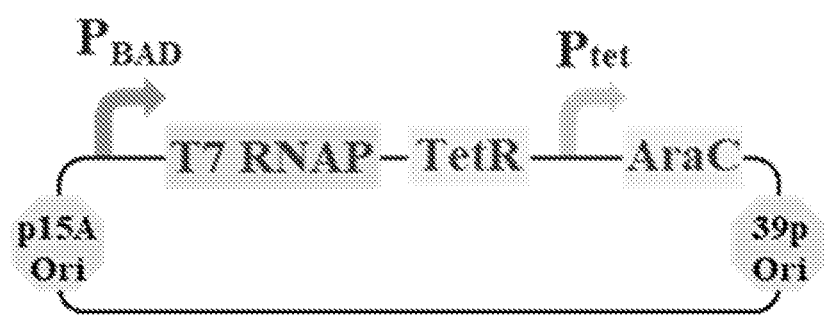
FIG. 2 illustrates a plot of the structure of the recombinant plasmid for regulating T7 RNAP expression, in accordance with embodiments.

The structure of the recombinant plasmid for regulating the expression of T7 RNAP is shown in FIG. 2.

Figure 3:
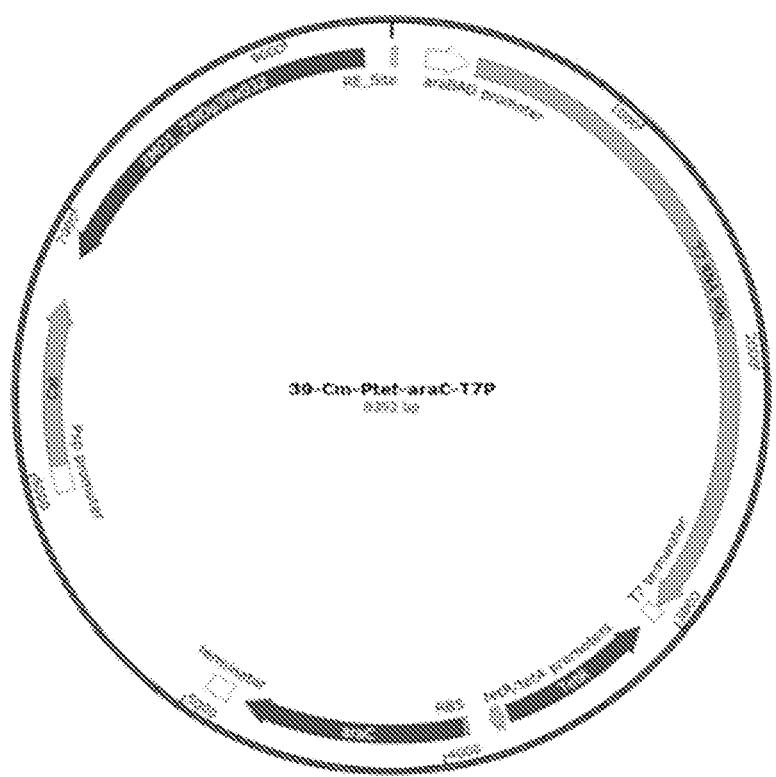
FIG. 3 illustrates a design diagram of the construction of the plasmid p39-Ptet-araC-T7P-Cm, in accordance with embodiments.

As shown in FIG. 3, the T7 RNAP encoding gene has been constructed into the shuttle plasmid pZM39, and the recombinant plasmid p39-Ptet-araC-T7P-Cm has been obtained.

Step 2

In some embodiments, the final strain was established by transforming the above recombinant plasmid into the receptive cells of *Zymomonas mobilis* (ZM4).

In some embodiments, ZM4 receptive cells were placed on ice. After the receptive cells melted, 50 μL was added into the pre-cooled electric cup, and 500 ng plasmid was added into the cup. The condition of transforming included 1.8 kV, 25 μF and 200Ω.

After electroporation, the cells were resuscitated in RMG5 liquid medium in an incubator at 30° C.

Culture resuscitated for 6~12 hours was centrifuged at 6000 rpm for 1 min to remove the 900 μL supernatant. The precipitate was suspended with the remaining 150 μL mediums, and coated with RC chloramphenicol resistant plate (120 μg/mL), and cultivated at 30° C. for 2 days. After 2 days, monocolonies were selected and verified by PCR.

Figure 4:
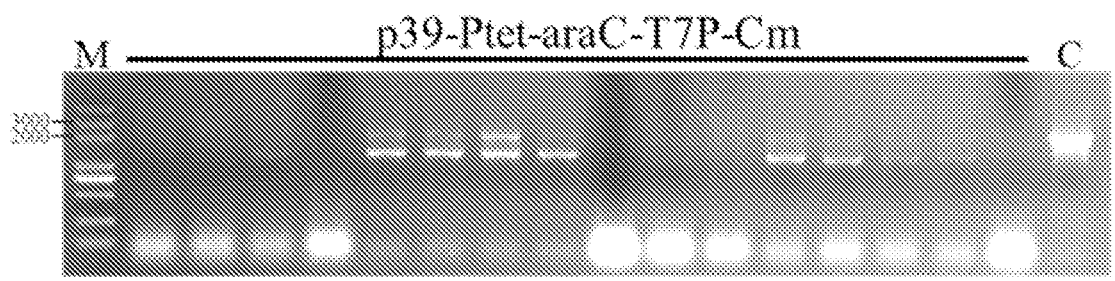
FIG. 4 illustrates the results of gel electrophoresis after electroporation of the recombinant plasmid into strain ZM4, in accordance with embodiments.

The gel electrophoresis results of recombinant plasmid electro-transferred into strain ZM4 are shown in FIG. 4.

Step 3

The strain obtained in the previous step was prepared into receptive cells. The process includes:
(1) Select the correct colonies, inoculate into bacterial jars which is containing about 10 mL RC (Cm: 120 μg/mL) liquid medium, and cultivated overnight at 30° C. (different volumes of medium could be set to ensure the logarithmic phase of the activated bacterial solution the next day).

(2) Transfer appropriate amount of bacterial solution in logarithmic phase to 200 mL RC (Cm: 120 g/mL) liquid medium in 500 mL triangulation bottles (40% bottling volume), control the initial $OD_{600\ nm}$ for 0.025~0.05, and cultivate at 30° C. with 100 rpm until the $OD_{600\ nm}$ up to 0.3~0.5 (about 4~6 h). When there are a few bubbles floating, $OD_{600\ nm}$ is almost up to 0.3~0.5. Whatever, the appropriate OD is 0.3~0.4 after about 4~5 hours of cultivation.

(3) Collect the bacterial cells by four 50 mL round-bottomed centrifuge tubes, centrifuge at 25° C. and 4000 rpm for 10 min; and pour away the supernatant carefully on a microbial ultra clean workbench.

(4) Add about 5 mL sterilized water to each tube to resuspend cell precipitate, concentrate 4 tubules in a centrifuge tube, replenish to 40 mL with sterile water, resuspend and wash precipitate; prepare another centrifugal tube of equal weight and centrifuge together with it; centrifuge at 25° C. and 4000 rpm for 10 min; and pour away the supernatant carefully on a microbial ultra clean workbench.

(5) Resuspend and wash the precipitate with 40 mL 10% glycerin, centrifuge at 25° C. and 4,000 rpm for 10 min; and pour away the supernatant carefully on a microbial ultra clean workbench.

(6) Repeat step (5) above once.

(7) Resuspend the precipitate with 200 μL 10% glycerol; divide into each one 1 mm electric cup for 50 μL bacterial solution with the cell concentration of $10^{10}$~$10^{11}$.

(8) Test the conversion efficiency of receptive cells and determine whether they are infected with other micro-organisms.

Step 4

Embodiments provided expression plasmid (pTZ series plasmids) that are able to be transformed into both *Zymomonas mobilis* (ZM4) and *Escherichia coli*. The expression plasmid (pTZ series plasmids) has been constructed by adding a Zymo-replicon from *Zymomonas mobilis* (ZM4) to pET vectors (e.g., pET22b, pET28a).

On account of different species have the different frequency of degenerate codon use, they are favorable to different degenerate codon. For example, the BamHl recognition sequence for pET22b and pET28 is different, the BamHl recognition sequence for pTZ28a is GGA triple codon, whereas pTZ22b is GAT.

In some embodiments, shuttle plasmids suitable for *Zymomonas mobilis* were constructed based on pET22b and pET28a, and the effect of target protein expression by *Zymomonas mobilis* that has been transformed the shuttle plasmids was compared.

Figure 5:
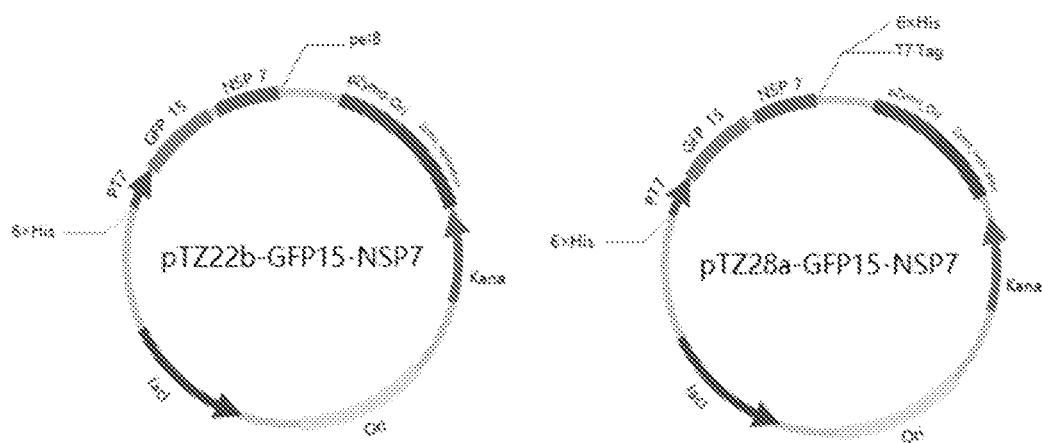
FIG. 5 illustrates a design diagram of pTZ series plasmids, in accordance with embodiments.

The structural maps of the shuttle plasmids, including pTZ28a-GFP15-NSP7 and pTZ22b-GFP15-NSP7, are shown in FIG. 5.

Examples use the following nucleotide sequence of a Zymo-replicon (pZymo_Ori) derived from *Zymomonas mobilis*.

> pZymo_Ori
SEQ ID NO. 6
acggtgagctggtgacctgccttatctctttccccagtagctaaaaata gggtggctttgcccgtgtatataaccaacagctttctcatggttttcc gaggcaggattcaacgaatttccccactaggaagaactaagaaagggaa -continued
tcgtgaaaatatccctaaaatagggaagtcgattttcagaatctgtgaa ggggtctatcaatattgattaaaccgtctatcaaaaaaaggggtaaaat tgatagaccttgcctcattcgatgaataggtataatcaaaaaatgtggt tttttttgattaaaggtttatcaaatatggcgacaaaattgagaaagcag ccaatcagatatgacgagaatcctttcatcgaaggtatggttgtgccag ttaaaagtcagagggttcagttatctcgattaggacgagatgataacat tctggtcaatcaagccactggtgagatgcaaggcactcatgtgacgact tacagacgtgttgatagtgaagaatttgtaaaattatttagcaccaata tcgcgctaacttttgaactaggagccgctggaataaaagctttcagcgt tctggtttggatacttcaagacaaaggcatcagcaaagacctcgtccct ttagacaaattcgttttagaggactttcttaacgcacaagaaaaaaac tggcactatctcaagctacctttgcaagaggtctagccgaattagaaaa agctaaaatcattgcaaagcatgttcgccaaggatggtattttattaat cctaatttcgttttcaatggcgaccgcgtagctttcacaacagttatag aacgcaaaaagacgctccaaaagcaagacgaatcagaataa, Examples use the following primer pairs (zymo-ori-F, zymo-ori-R) to amplify the Zymo-replicon from *Zymomonas mobilis*:

zymo-ori-F:
SEQ ID NO. 19
acggtgagctggtgacctg, zymo-ori-R:
SEQ ID NO. 20
gaaaagtgccacctgttattctgattcgtcttgcttttggagcg, In some embodiments, the f1 origin of pET22b and the f1 origin of pET28a were respectively replaced by the Zymo-replicon (pZymo_Ori). The process included:

(1) Amplify the reverse fragment of pET22b by the primers 22b-FK-F and 22b-FK-R; and amplify the reverse fragment of pET28a by the primers 28a-FK-F and 28a-FK-R.

22b-FK-F:
SEQ ID NO. 21
caggtggcacttttcgggg,

226-FK-R:
SEQ ID NO. 22
gcaggtcaccagctcaccgtcccattcgccaatccggatatag,

28a-FK-F:
SEQ ID NO. 23
caggtggcacttttcgggga,

28a-FK-R:
SEQ ID NO. 24
gcaggtcaccagctcaccgtcccattcgccaatccggatatag, (2) Link the reverse fragment of pET22b with the Zymo-replicon (pZymo_Ori) by Gibson assembly to obtain the shuttle plasmid pTZ22b; link the reverse fragment of pET28a with the Zymo-replicon (pZymo_Ori) by Gibson assembly to obtain the shuttle plasmid pTZ28a.

(3) Replace the ampicillin resistance gene on pTZ22b by the kanamycin resistance gene on pTZ28a, to exclude the effect of different antibiotics on the gene expression. In this step, the linear vector of pTZ22b was obtained by a PCR reaction that was performed with pTZ22b as template, 22b-Anti-V-F and 22b-Anti-V-F as primer pairs. The fragment of kanamycin resistance gene was obtained by a PCR reaction that was performed with pTZ28a as template, Kana-F and Kana-R as primer pairs. Finally, pTZ22b was obtained by linking the linear vector of pTZ22b to the fragment of kanamycin resistance gene.

22b-Anti-V-F:
SEQ ID NO. 25
agctgtcaaacatgagaattctgtcagaccaagtttactcatatatact ttagattgat, 22b-Anti-V-R:
SEQ ID NO. 26
gaaaagtgccacctgttattctgattcgtcttgcttttggagcg, Kana-F:
SEQ ID NO. 27
caggtggcacttttcggggaaatgtgttagaaaaactcatcgagc, Kana-R:
SEQ ID NO. 28
aattctcatgtttgacagcttatcatcgatg, Step 5

Green fluorescent protein GFP was expressed by using pTZ series plasmids (e.g., pTZ22b, pTZ28a).

In this step, the vector of pTZ22b was obtained by a PCR amplification by using pTZ22b as templates, pTZ22b-F and pTZ22b-R as primers. The vector of pTZ28a was obtained by a PCR amplification by using pTZ28a as templates, pTZ28a-F and pTZ28a-R as primers. Recombinant plasmid pTZ22b-GFP15-NSP7 was obtained by Gibson assembly of the vector of pTZ22b with GFP15-NSP7 fragment. Recombinant plasmid pTZ28a-GFP15-NSP7 was obtained by Gibson assembly of the vector of pTZ28a with GFP15-NSP7 fragment. The fragment of GFP15-NSP7 was obtained by a PCR performed with sfGFP15-F and NSP7-R as primers, and the nucleotide sequence of SEQ ID NO.1 as template. And Recombinant plasmid pEZ15A-GFP15-NSP7 was obtained by Gibson assembly of the vector of pEZ15A with GFP15-NSP7 fragment. Sanger sequencing was used to determine the correct recombinant plasmids pTZ22b-GFP15-NSP7, pTZ28a-GFP15-NSP7 and pEZ15A-GFP15-NSP7.

Figure 6:
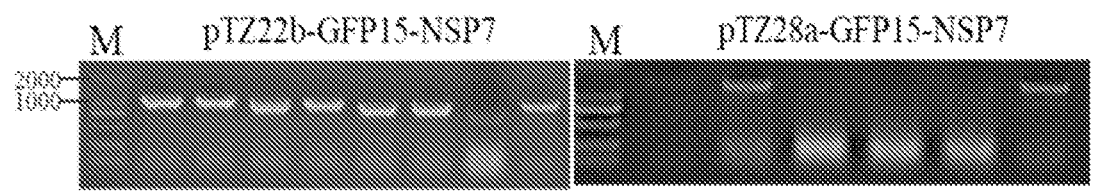
FIG. 6 illustrates the PCR gel electrophoresis of monocolonies of bacteria obtained from two plasmids, in accordance with embodiments.

FIG. 6 shows the agarose gel electrophoresis patterns of colonies transformed with pTZ22b-GFP15-NSP7 and pTZ28a-GFP15-NSP7, respectively.

pTZ22b-F:
SEQ ID NO. 29
gcaaccttacaataactcgagcaccaccaccaccactg, pTZ22b-R:
SEQ ID NO. 30
ctcgcccttgctcacatgatgatgatgatggtgcatatg, pTZ28a-F:
SEQ ID NO. 31
gcaaccttacaataactcgagcaccaccaccaccactg, pTZ28a-R:
SEQ ID NO. 32
gcccttgctcaccatgatgatgatgatgatggctgc, -continued >GFP15-NSP7
SEQ ID NO. 5
atggtgagcaagggcgaggagctgttcaccggggtggtgcccatcctgg tcgagctggacggcgacgtaaacggccacaagttcagcgtgcgcggcga gggcgagggcgatgccaccaacggcaagctgaccctgaagttcatctgc accaccggcaagctgcccgtgccctggcccaccctcgtgaccaccctga cctacggcgtgcagtgcttcagccgctaccccgaccacatgaagcagca cgacttcttcaagtccgccatgcccgaaggctacgtccaggagcgcacc atcagcttcaaggacgacggcacctacaagacccgcgccgaggtgaagt tcgagggcgacaccctggtgaaccgcatcgagctgaagggcatcgactt caaggaggacggcaacatcctggggcacaagctggagtacaacttcaac agccacaacgtctatatcaccgccgacaagcagaagaacggcatcaagg ccgaatttgaaattcgtcataatgtggaagatggcagcgtgcagctggc ggatcattatcagcagaataccccgattggcgatggcccagtgctgctg ccggatgaccactatctgagcaccgaaagcgtgctgagcaaagatccga atgaagatcgtgatcatatggtcctgctggaatttgtgaccgcggcagg cattgatctgggcatggatgaactgtataaattggaggttttgttccag ggtccatctaaaatgtcagatgtaaagtgcacatcagtagtcttactct cagttttgcaacaactcagagtagaatcatcatctaaattgtgggctca atgtgtccagttacacaatgacattctcttagctaaagatactactgaa gcctttgaaaaaatggtttcactactttctgttttgctttccatgcagg gtgctgtagacataaacaagctttgtgaagaaatgctggacaacagggc aaccttacaataa, sfGFP15-F:
SEQ ID NO. 33
gtgagcaagggcgaggag, NSP7-R:
SEQ ID NO. 34
ttattgtaaggttgccctgttgtcc, Step 6

In this step, the pTZ22b-GFP15-NSP7, pTZ28a-GFP15-NSP7 and control plasmid (pEZ15A-GFP15-NSP7) were respectively electro-transformed into the competent cells of *Zymomonas mobilis*, and then RCK plates (Cm: 120 μg/mL; Km: 200 μg/mL) were used for screening. Among them, the control plasmid had no T7 promoter and no T7 terminator compared to pTZ22b-GFP15-NSP7 and pTZ28a-GFP15-NSP7.

Step 7

In this step, the performance of the T7 expression system was tested by tetracycline and arabinose that were used as inducers.

In this step, the verified colonies were incubated with RCK plates (Cm: 120 g/mL; Km: 200 μg/mL), and cultured at 30° C. and 100 rpm in medium containing different concentrations of tetracycline (Tc) and arabinose (Ara) (e.g. 0.8 Tc/3Ara is 0.8 μg/mL tetracycline+3% arabinose). Among them, three parallels were set for each sample and each gradient.

After cultivating to logarithmic phase, each 200 μL bacterial solution sample was centrifuged at 12,000 rpm for 1 min, removed supernatant, washed cell precipitate and resuspended twice with 1×PBS. And the fluorescence intensity was measured by flow cytometry using a preset program, that the cell collection event was set to 20,000 in order to prevent small probabilities and accidental events.

The expression genes levels (fluorescence intensity) of pTZ22b-GFP15-NSP7, pTZ28a-GFP15-NSP7 and pEZ15A-GFP15-NSP7 were tested to examine the performance of the T7 expression system in Zymomonas mobilis.

Step 8

According to the data obtained by flow cytometry, the average fluorescence value of GFP15 for all events was taken for each sample and calculated to exclude the influence of errors from the outside.

Figure 7:
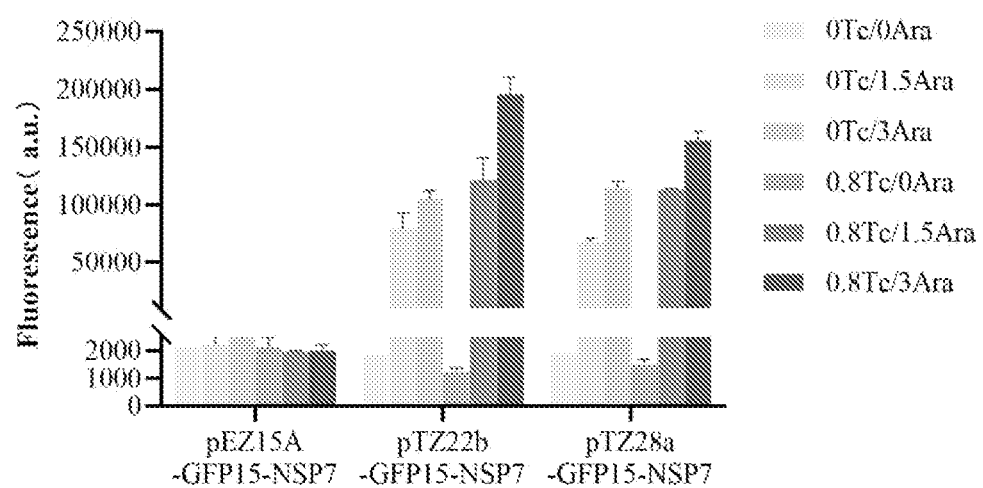
FIG. 7 illustrates the fluorescence intensity of a control strain and a mutant strain at exponential and stationary phases.

The fluorescence intensity values of the control strain and the mutant strain, respectively in the exponential phase and the stationary phase, are shown in FIG. 7, wherein the X-axis represents the name of the protein expression plasmid, and the Y-axis represents the fluorescence intensity values.

FIG. 7 also shows that pEZ15A-GFP15-NSP7, pTZ22b-GFP15-NSP7, and pTZ28a-GFP15-NSP7 can be detected by fluorescence intensity. The fluorescence intensity of pTZ22b-GFP15-NSP7 and pTZ28a-GFP15-NSP7 are much higher than that of pEZ15A-GFP15-NSP7.

Figure 8:
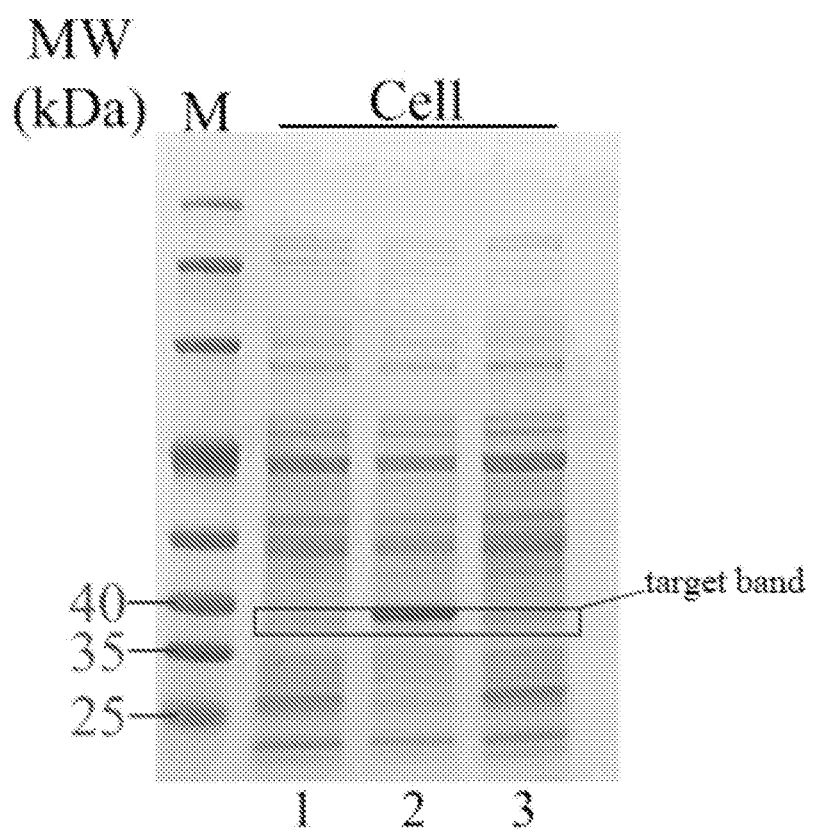
FIG. 8 illustrates the SDS-PAGE diagram of three plasmids expressed in *Zymomonas mobilis*. 1: pEZ15A-GFP15-NSP7, 2: pTZ22b-GFP15-NSP7, 3: pTZ28a-GFP15-NSP7.

FIG. 8 shows that expression in pTZ22b-GFP15-NSP7 is the highest among the three plasmids, that is consistent with the results of flow cytometry. pTZ22b-GFP15-NSP7, pTZ28a-GFP15-NSP7 and pEZ15A-GFP15-NSP7 are simultaneously expressed in the test strain ZM-1 (p39-Ptet-Arac-T7P) with the expected size of 36 kDa. The protein expression has been detected by SDS-PAGE.

The results have showed that the T7 expression system plays a crucial role in Zymomonas mobilis, and both pTZ22b and pTZ28a are expressed normally. In the presence of tetracycline or arabinose alone, the amount of protein expression is similar to that in the control expression plasmid pEZ15A-GFP-NSP7. Due to the leaky expression in Ptet, after the addition of arabinose, T7 RNAP is expressed, which induces the expression in the target gene for about 35 folds higher than the control plasmid. When the expression in araC is further induced by adding tetracycline, the expression in the target gene has been enhanced by 1 to 2 folds compared with arabinose alone. The highest expression in araC is realized with an inducer gradient of 0.8 Tc/3Ara, that is 55 to 85 folds higher than the control plasmid.

The results have shown that when tetracycline and arabinose used as two inducers are present at the same time, the fluorescence intensity is higher than that of the control group, in other words, the target protein GFP expression is higher. In the absence of arabinose, the target protein GFP is not expressed or expressed at very low levels. The experimental results have shown that the T7 expression system is successfully established in Zymomonas mobilis, and the tight regulation for gene and circuit as well as protein expression are also achieved.

The above is only the preferred embodiments of this disclosure and is not intended to limit this disclosure. Any modification, equivalent replacement, improvement, etc., made within the spirit and principle of this disclosure shall be included in the scope of this disclosure.

What is claimed is:

1. A construction method of a regulation system for gene expression in *Zymomonas mobilis*, comprising:
    constructing a recombinant plasmid for regulating T7 RNAP expression; and
    constructing a shuttle plasmid for expressing genes to be driven by a T7 promoter;
    wherein the construction method of the recombinant plasmid comprises:
        amplifying fragments of T7 RNAP, $P_{BAD}$, araC, and TetR+Ptet successively;
        reversely amplifying a plasmid pZM39 by using primers 39p-F and 39p-R to obtain a vector of pZM39, wherein the primers 39p-F and 39p-R comprise SEQ ID NO.15 and SEQ ID NO.16, respectively;
        ligating the vector of pZM39 with the fragments of T7 RNAP, $P_{BAD}$, araC, TetR+Ptet successively;
        transferring ligation product into *Escherichia coli* DH5α competent cells and selecting positive colonies by using chloramphenicol resistant plates;
        verifying to obtain positive transformants by using primers pEZ-dp-F comprising SEQ ID NO.17 that is: ctgaattcgcggccgc and pEZ-15A-R comprising SEQ ID NO.18 that is: cacttcactgacaccctcat; and
        cultivating and extracting the positive transformants to obtain the recombinant plasmid;
    wherein a nucleotide sequence of the T7 RNAP comprises SEQ ID NO.1;
    a nucleotide sequence of the $P_{BAD}$ comprises SEQ ID NO.2;
    a nucleotide sequence of the araC comprises SEQ ID NO.3;
    a nucleotide sequence of the TetR+Ptet comprises SEQ ID NO.4;
    primers for amplifying a fragment of the T7 RNAP are named T7 RNAP-F and T7 RNAP-R, wherein a nucleotide sequence of the T7 RNAP-F comprises SEQ ID NO.7 that is:

atgaacacgattaacatcgctaagaac and a nucleotide sequence of the T7 RNAP-R comprises SEQ ID NO.8 that is:

agtagtaggttgaggccgttga;

primers for amplifying a fragment of the $P_{BAD}$ are named $P_{BAD}$-F and $P_{BAD}$-R, wherein a nucleotide sequence of the $P_{BAD}$-F comprises SEQ ID NO.9 that is:

cggccgcttctagagaaaccaattgtccatattgcatcagacattg and a nucleotide sequence of the $P_{BAD}$-R comprises SEQ ID NO.10 that is:

gatgttaatcgtgttcatgggagatcctttctcctctttag;

primers for amplifying a fragment of the araC are named araC-F and araC-R, wherein a nucleotide sequence of the araC-F comprises SEQ ID NO. 11 that is:

atggctgaagcgcaaaatgatcc and a nucleotide sequence of the araC-R comprises SEQ ID NO. 12 that is:

ctcgagatctatgggacgttatgacaacttgacggctacatcattc;

and
    primers for amplifying a fragment of TetR+Ptet are named TetR-F and Ptet-R, wherein a nucleotide sequence of the TetR-F comprises SEQ ID NO. 13 that is:

cctcaacctactactttaagacccactttcacatttaagttgttttct
    aa and a nucleotide sequence of the Ptet-R comprises SEQ ID NO. 14 that is:

```
ttgcgcttcagccatgggagatcctttctcctctttagatc;
``` wherein the shuttle plasmid has a replicon derived from *Zymomonas mobilis* and a replicon derived from *Escherichia coli;* the shuttle plasmid is obtained by replacing f1 origin on plasmid pET22b or pET28a from *Escherichia coli* with a Zymo-replicon derived from *Zymomonas mobilis*, and inserting a gene fragment to be driven by the T7 promoter.

2. The construction method of claim 1, wherein a resistance gene of the plasmid pET22b has been replaced with a kanamycin resistance gene.

* * * * *

SEQUENCE LISTING

```
Sequence total quantity: 34
SEQ ID NO: 1            moltype = DNA  length = 2652
FEATURE                 Location/Qualifiers
source                  1..2652
                        mol_type = genomic DNA
                        organism = unidentified
SEQUENCE: 1
atgaacacga ttaacatcgc taagaacgac ttctctgaca tcgaactggc tgctatcccg 60
ttcaacactc tggctgacca ttacggtgag cgtttagctc gcgaacagtt ggcccttgag 120
catgagtctt acgagatggg tgaagcacgc ttccgcaaga tgtttgagcg tcaacttaaa 180
gctggtgagg ttgcggataa cgctgccgcc aagcctctca tcactaccct actccctaag 240
atgattgcac gcatcaacga ctggtttgag gaagtgaaag ctaagcgcgg caagcgcccg 300
acagccttcc agttcctgca agaaatcaag ccggaagccg tagcgtacat caccattaag 360
accactctgg cttgcctaac cagtgctgac aatacaaccg ttcaggctgt agcaagcgca 420
atcggtcggg ccattgagga cgaggctcgc ttcggtcgta tccgtgacct tgaagctaag 480
cacttcaaga aaaacgttga ggaacaactc acaaagcgcg tagggcacgt ctacaagaaa 540
gcatttatgc aagttgtcga ggctgacatg ctctctaagg gtctactcgg tggcgaggcg 600
tggtcttcgt ggcataagga agactctatt catgtaggag tacgctgcat cgagatgctc 660
attgagtcaa ccggaatggt tagcttacac cgccaaaatg ctggcgtagt aggtcaagac 720
tctgagacta tcgaactcgc acctgaatac gctgaggcta tcgcaacccg tacaggtgcg 780
ctggctgcca tctctccgat gttccaacct tgcgtagttc ctcctaagcc gtggactggc 840
attactggtg gtgctattg ggctaacggt cgtcgtcctc tggcgctggt gcgtactcac 900
agtaagaaag cactgatgcg ctacgaagac gtttacatgc ctgaggtgta caaagcgatt 960
aacattgcgc aaaacaccgc atggaaaatc aacaagaaag tcctagcggt cgccaacgta 1020
atcaccaagt ggaagcattg tccggtcgag gacatccctg cgattgagcg tgaagaactc 1080
ccgatgaaac cggaagacat cgacatgaat cctgaggctc tcaccgcgtg gaaacgtgct 1140
gccgctgctg tgtaccgcaa ggacaaggct cgcaagtctc gccgtatcag ccttgagttc 1200
atgcttgagc aagccaataa gtttgctaac cataaggcca tctggttccc ttacaacatg 1260
gactggcgcg gtcgtgttta cgctgtgtca atgttcaacc cgcaaggtaa cgatatgacc 1320
aaaggactgc ttacgctggc gaaaggtaaa ccaatcggta aggaaggtta ctactggctg 1380
aaaatccacg gtgcaaactg tgcgggtgtc gataaggttc cgttccctga gcgcatcaag 1440
ttcattgagg aaaaccacga gaacatcatg gcttgcgcta agtctccact ggagaacact 1500
tggtgggctg agcaagattc tccgttctgc ttccttgcgt tctgctttga gtacgctggg 1560
gtacagcacc acggcctgag ctataactgc tccttccgc tggcgtttga cgggtcttgc 1620
tctggcatcc agcacttctc cgcgatgctc cgagatgagg taggtggtcg cgcggttaac 1680
ttgcttccta gtgaaaccgt tcaggacatc tacgggattg ttgctaagaa agtcaacgag 1740
attctgcagg ctgatgctat caacgggacc gataacgaag tagttaccgt gaccgatgag 1800
aacactggtg aaatctctga gaaagtcaag ctgggcacta aggcactggc tggtcaatgg 1860
ctggcttacg gtgttactcg cagtgtgact aagcgttcag tcatgacgct ggcttacggg 1920
```

```
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ccgtttccgt taccgttgtt gctgctgttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggttvcc ctgtgtggca ggaatacaag   2220
aagcctattc agacgcgctt gaacctgatg ttcctcggtc agttccgctt acagcctacc   2280
attaacacca caaagatag cgagattgat gcacacaaac aggagtctgg tatcgctcct   2340
aactttgtac acagccaaga cggtagccac cttcgtaaga ctgtagtgtg ggcacacgag   2400
aagtacggaa tcgaatcttt tgcactgatt cacgactcct tcggtaccat tccggctgac   2460
gctgcgaacc tgttcaaagc agtgcgcgaa actatggttg acacatatga gtcttcgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aa                                                       2652

SEQ ID NO: 2            moltype = DNA   length = 320
FEATURE                 Location/Qualifiers
source                  1..320
                        mol_type = other DNA
                        organism = unidentified
SEQUENCE: 2
aaaccaattg tccatattgc atcagacatt gccgtcactg cgtctttac tggctcttct     60
cgctaaccaa accggtaacc ccgctttatta aaagcattct gtaacaaagc gggaccaaag  120
ccatgacaaa aacgcgtaac aaaagtgtct ataatcacgg cagaaaagtc cacattgatt   180
atttgcacgg cgtcacactt tgctatgcca tagcattttt atccataaga ttagcggatc   240
ctacctgacg cttttatcg caactctcta ctgtttctcc ataagtattc aaatgatcta    300
aagaggagaa aggatctccc                                                320

SEQ ID NO: 3            moltype = DNA   length = 879
FEATURE                 Location/Qualifiers
source                  1..879
                        mol_type = genomic DNA
                        organism = unidentified
SEQUENCE: 3
atggctgaag cgcaaaatga tccccctgctg ccgggatact cgtttaatgc ccatctggtg   60
gcgggtttaa cgccgattga ggccaacggt tatctcgatt tttttatcga ccgaccgctg   120
ggaatgaaag gttatattct caatctcacc attcgcggtc aggggtggt gaaaaatcag    180
ggacgagaat ttgtttgccg accgggtgat attttgctgt tcccgccagg agagattcat   240
cactacggtc gtcatccgga ggctcgcgaa tggtatcacc agtgggttta ctttcgtccg   300
cgcgcctact ggcatgaatg gcttaactgg ccgtcaatat ttgccaatac ggggttcttt   360
cgcccggatg aagcgcacca gccgcatttc agcgacctgt ttgggcaaat cattaacgcc   420
gggcaagggg aagggcgcta tcggagctg ctggcgataa atctgcttga gcaattgtta    480
ctgcggcgca tggaagcgat taacgagtcg ctccatccac cgatggataa tcgggtacgc   540
gaggcttgtc agtacatcag cgatcacctg gcagacagca attttgatat cgccagcgtc   600
gcacagcatg tttgcttgtc gccgtcgcgt ctgtcacatc ttttccgcca cagttaggg   660
attagcgtct taagctggcg cgaggaccaa cgtatcagcc aggcgaagct gcttttgagc   720
accaccgga tgcctatcgc caccgtcggt cgcaatgttg gttttgacga tcaactctat    780
ttctcgcggg tatttaaaaa atgcaccggg gccagcccga gcgagttccg tgccggttgt   840
gaagaaaaag tgaatgatgt agccgtcaag ttgtcataa                           879

SEQ ID NO: 4            moltype = DNA   length = 810
FEATURE                 Location/Qualifiers
source                  1..810
                        mol_type = other DNA
                        organism = unidentified
SEQUENCE: 4
ttaagaccca ctttcacatt taagttgttt ttctaatccg catatgatca attcaaggcc    60
gaataagaag gctggctctg caccttggtg atcaaataat tcgatagctt gtcgtaataa   120
tggcggcata ctatcagtag taggtgtttc ccttcttct ttagcgactt gatgctcttg    180
atcttccaat acgcaaccta aagtaaaatg ccccacagcc ctgagtgcat ataatgcatt   240
ctctagtgaa aaaccttgtt ggcataaaaa ggctaattga ttttcgagag tttcatactg   300
ttttttctgta ggccgtgtac ctaaatgtac tttttgctcca tcgcgatgac ttagtaaagc  360
acatctaaaa cttttagcgt tattacgtaa aaaatcttgc cagctttccc cttctaaagg   420
gcaaaagtga gtatggtgcc tatctaacat ctcaatggct aaggcgtcga gcaaagcccg   480
cttattttt acatgccaat acaatgtagg ctgctctaca cctacttct gggcgagttt     540
acgggttgtt aaaccttcga ttccgacctc attaagcagc tctaatgcgc tgttaatcac   600
tttacttta tctaatctag acatcattaa ttcctaattt tgttgacac tctatcgttg     660
atagagttat tttaccactc cctatcagtg atagagaaaa gtattcaaat gatcttccct   720
atcagtgata gagaaaagta ttcaaatgat cttcccctatc agtgatagag aaaagtattc  780
aaatgatcta aagaggagaa aggatctccc                                     810

SEQ ID NO: 5            moltype = DNA   length = 993
FEATURE                 Location/Qualifiers
source                  1..993
                        mol_type = other DNA
                        organism = unidentified
SEQUENCE: 5
atggtgagca agggcgagga gctgttcacc ggggtggtgc ccatcctggt cgagctggac    60
ggcgacgtaa acggccacaa gttcagcgtg tcgggcgagg gcgagggcga tgccaccaac   120
ggcaagctga ccctgaagtt catctgcacc accggcaagc tgcccgtgcc ctggcccacc   180
```

```
ctcgtgacca ccctgaccta cggcgtgcag tgcttcagcc gctaccccga ccacatgaag    240
cagcacgact tcttcaagtc cgccatgccc gaaggctacg tccaggagcg caccatcagc    300
ttcaaggacg acggcaccta caagacccgc gccgaggtga agttcgaggg cgacaccctg    360
gtgaaccgca tcgagctgaa gggcatcgac ttcaaggagg acggcaacat cctggggcac    420
aagctggagt acaacttcaa cagccacaac gtctatatca ccgccgacaa gcagaagaac    480
ggcatcaagg ccgaatttga aattcgtcat aatgtggaag atggcagcgt gcagctggcc    540
gatcattatc agcagaatac cccgattggc gatggcccag tgctgctgcc ggatgaccac    600
tatctgagca ccgaaagcgt gctgagcaaa gatccgaatg aagatcgtga tcatatggtc    660
ctgctggaat ttgtgaccgc ggcaggcatt gatctgggca tggatgaact gtataaattg    720
gaggttttgt tccagggtcc atctaaaatg tcagatgtaa agtgcacatc agtagtctta    780
ctctcagttt tgcaacaact cagagtagaa tcatcatcta aattgtgggc tcaatgtgtc    840
cagttacaca atgacattct cttagctaaa gatactactg aagcctttga aaaaatggtt    900
tcactacttt ctgttttgct ttccatgcag ggtgctgtag acataaacaa gctttgtgaa    960
gaaatgctgg acaacagggc aaccttacaa taa                                993

SEQ ID NO: 6           moltype = DNA   length = 874
FEATURE                Location/Qualifiers
source                 1..874
                       mol_type = other DNA
                       organism = unidentified
SEQUENCE: 6
acggtgagct ggtgacctgc cttatctctt tccccagtag ctaaaaatag ggtggctttg     60
cccgtgtata taaccaacag cttttctcatg gttttttccga ggcaggattc aacgaatttc    120
cccactagga agaactaaga aagggaatcg tgaaaatatc cctaaaaatag ggaagtcgat    180
tttcagaatc tgtgaagggg tctatcaata ttgattaaac cgtctatcaa aaaaaggggt    240
aaaattgata gaccttgcct cattcgatga ataggtataa tcaaaaaatg tggttttttt    300
gattaaaggt ttatcaaata tggcgacaaa attgagaaag cagccaatca gatatgacga    360
gaatcctttc atcgaaggta tggttgtgcc agttaaaagt cagagggttc agttatctcg    420
attaggacga gatgataaca ttctggtcaa tcaagccact ggtgagatgc aaggcactca    480
tgtgacgact tacagacgtg ttgatagtga agaatttgta aaattattta gcaccaatat    540
cgcgctaact tttgaactag gagccgctgg aataaaagct ttcagcgttc tggtttggat    600
acttcaagac aaaggcatca gcaaagacct cgtccctttta gacaaattcg ttttagagga    660
cttttcttaac gcaagagaa aaaaactggc actatctcaa gctacctttg caagaggtct    720
agccgaatta gaaaaagcta aaatcattgc aaagcatgtt cgccaaggat ggtatttat    780
taatcctaat ttcgttttca atggcgaccg cgtagctttc acaacagtta tagaacgcaa    840
aaagacgctc caaaagcaag acgaatcaga ataa                               874

SEQ ID NO: 7           moltype = DNA   length = 27
FEATURE                Location/Qualifiers
source                 1..27
                       mol_type = other DNA
                       organism = synthetic construct
SEQUENCE: 7
atgaacacga ttaacatcgc taagaac                                        27

SEQ ID NO: 8           moltype = DNA   length = 22
FEATURE                Location/Qualifiers
source                 1..22
                       mol_type = other DNA
                       organism = synthetic construct
SEQUENCE: 8
agtagtaggt tgaggccgtt ga                                             22

SEQ ID NO: 9           moltype = DNA   length = 46
FEATURE                Location/Qualifiers
source                 1..46
                       mol_type = other DNA
                       organism = synthetic construct
SEQUENCE: 9
cggccgcttc tagagaaacc aattgtccat attgcatcag acattg                   46

SEQ ID NO: 10          moltype = DNA   length = 41
FEATURE                Location/Qualifiers
source                 1..41
                       mol_type = other DNA
                       organism = synthetic construct
SEQUENCE: 10
gatgttaatc gtgttcatgg gagatccttt ctcctctttta g                       41

SEQ ID NO: 11          moltype = DNA   length = 23
FEATURE                Location/Qualifiers
source                 1..23
                       mol_type = other DNA
                       organism = synthetic construct
SEQUENCE: 11
atggctgaag cgcaaaatga tcc                                            23
```

-continued

```
SEQ ID NO: 12            moltype = DNA   length = 46
FEATURE                  Location/Qualifiers
source                   1..46
                         mol_type = other DNA
                         organism = synthetic construct
SEQUENCE: 12
ctcgagatct atgggacgtt atgacaactt gacggctaca tcattc                    46

SEQ ID NO: 13            moltype = DNA   length = 51
FEATURE                  Location/Qualifiers
source                   1..51
                         mol_type = other DNA
                         organism = synthetic construct
SEQUENCE: 13
cctcaaccta ctactttaag acccactttc acatttaagt tgtttttcta a              51

SEQ ID NO: 14            moltype = DNA   length = 41
FEATURE                  Location/Qualifiers
source                   1..41
                         mol_type = other DNA
                         organism = synthetic construct
SEQUENCE: 14
ttgcgcttca gccatgggag atcctttctc ctctttagat c                         41

SEQ ID NO: 15            moltype = DNA   length = 19
FEATURE                  Location/Qualifiers
source                   1..19
                         mol_type = other DNA
                         organism = synthetic construct
SEQUENCE: 15
cgtcccatag atctcgagc                                                  19

SEQ ID NO: 16            moltype = DNA   length = 17
FEATURE                  Location/Qualifiers
source                   1..17
                         mol_type = other DNA
                         organism = synthetic construct
SEQUENCE: 16
ctctagaagc ggccgcg                                                    17

SEQ ID NO: 17            moltype = DNA   length = 16
FEATURE                  Location/Qualifiers
source                   1..16
                         mol_type = other DNA
                         organism = synthetic construct
SEQUENCE: 17
ctgaattcgc ggccgc                                                     16

SEQ ID NO: 18            moltype = DNA   length = 20
FEATURE                  Location/Qualifiers
source                   1..20
                         mol_type = other DNA
                         organism = synthetic construct
SEQUENCE: 18
cacttcactg acaccctcat                                                 20

SEQ ID NO: 19            moltype = DNA   length = 19
FEATURE                  Location/Qualifiers
source                   1..19
                         mol_type = other DNA
                         organism = synthetic construct
SEQUENCE: 19
acggtgagct ggtgacctg                                                  19

SEQ ID NO: 20            moltype = DNA   length = 44
FEATURE                  Location/Qualifiers
source                   1..44
                         mol_type = other DNA
                         organism = synthetic construct
SEQUENCE: 20
gaaaagtgcc acctgttatt ctgattcgtc ttgcttttgg agcg                      44

SEQ ID NO: 21            moltype = DNA   length = 19
FEATURE                  Location/Qualifiers
source                   1..19
                         mol_type = other DNA
                         organism = synthetic construct
SEQUENCE: 21
caggtggcac ttttcgggg                                                  19
```

| | | |
|---|---|---|
| SEQ ID NO: 22<br>FEATURE<br>source | moltype = DNA   length = 43<br>Location/Qualifiers<br>1..43<br>mol_type = other DNA<br>organism = synthetic construct | |
| SEQUENCE: 22<br>gcaggtcacc agctcaccgt cccattcgcc aatccggata tag | | 43 |
| SEQ ID NO: 23<br>FEATURE<br>source | moltype = DNA   length = 20<br>Location/Qualifiers<br>1..20<br>mol_type = other DNA<br>organism = synthetic construct | |
| SEQUENCE: 23<br>caggtggcac ttttcgggga | | 20 |
| SEQ ID NO: 24<br>FEATURE<br>source | moltype = DNA   length = 43<br>Location/Qualifiers<br>1..43<br>mol_type = other DNA<br>organism = synthetic construct | |
| SEQUENCE: 24<br>gcaggtcacc agctcaccgt cccattcgcc aatccggata tag | | 43 |
| SEQ ID NO: 25<br>FEATURE<br>source | moltype = DNA   length = 59<br>Location/Qualifiers<br>1..59<br>mol_type = other DNA<br>organism = synthetic construct | |
| SEQUENCE: 25<br>agctgtcaaa catgagaatt ctgtcagacc aagtttactc atatatactt tagattgat | | 59 |
| SEQ ID NO: 26<br>FEATURE<br>source | moltype = DNA   length = 44<br>Location/Qualifiers<br>1..44<br>mol_type = other DNA<br>organism = synthetic construct | |
| SEQUENCE: 26<br>gaaaagtgcc acctgttatt ctgattcgtc ttgcttttgg agcg | | 44 |
| SEQ ID NO: 27<br>FEATURE<br>source | moltype = DNA   length = 45<br>Location/Qualifiers<br>1..45<br>mol_type = other DNA<br>organism = synthetic construct | |
| SEQUENCE: 27<br>caggtggcac ttttcgggga aatgtgttag aaaaactcat cgagc | | 45 |
| SEQ ID NO: 28<br>FEATURE<br>source | moltype = DNA   length = 31<br>Location/Qualifiers<br>1..31<br>mol_type = other DNA<br>organism = synthetic construct | |
| SEQUENCE: 28<br>aattctcatg tttgacagct tatcatcgat g | | 31 |
| SEQ ID NO: 29<br>FEATURE<br>source | moltype = DNA   length = 41<br>Location/Qualifiers<br>1..41<br>mol_type = other DNA<br>organism = synthetic construct | |
| SEQUENCE: 29<br>gcaaccttac aataactcga gcaccaccac caccaccact g | | 41 |
| SEQ ID NO: 30<br>FEATURE<br>source | moltype = DNA   length = 39<br>Location/Qualifiers<br>1..39<br>mol_type = other DNA<br>organism = synthetic construct | |
| SEQUENCE: 30<br>ctcgcccttg ctcacatgat gatgatgatg gtgcatatg | | 39 |
| SEQ ID NO: 31<br>FEATURE<br>source | moltype = DNA   length = 41<br>Location/Qualifiers<br>1..41<br>mol_type = other DNA<br>organism = synthetic construct | |

```
SEQUENCE: 31
gcaaccttac aataactcga gcaccaccac caccaccact g                                41

SEQ ID NO: 32           moltype = DNA  length = 38
FEATURE                 Location/Qualifiers
source                  1..38
                        mol_type = other DNA
                        organism = synthetic construct
SEQUENCE: 32
gcccttgctc accatgtgat gatgatgatg atggctgc                                    38

SEQ ID NO: 33           moltype = DNA  length = 18
FEATURE                 Location/Qualifiers
source                  1..18
                        mol_type = other DNA
                        organism = synthetic construct
SEQUENCE: 33
gtgagcaagg gcgaggag                                                          18

SEQ ID NO: 34           moltype = DNA  length = 25
FEATURE                 Location/Qualifiers
source                  1..25
                        mol_type = other DNA
                        organism = synthetic construct
SEQUENCE: 34
ttattgtaag gttgccctgt tgtcc                                                  25
```